United States Patent
Mackin

(10) Patent No.: US 6,905,457 B2
(45) Date of Patent: Jun. 14, 2005

(54) RADIANT FIELD MANAGEMENT FOR INFANT CARE APPARATUS

(75) Inventor: Michael H. Mackin, Ellicott City, MD (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/282,970

(22) Filed: Oct. 29, 2002

(65) Prior Publication Data

US 2004/0082829 A1 Apr. 29, 2004

(51) Int. Cl.⁷ .............................................. A61G 11/00
(52) U.S. Cl. ....................................................... 600/22
(58) Field of Search ..................................... 600/21–22

(56) References Cited

U.S. PATENT DOCUMENTS

| | | | |
|---|---|---|---|
| 4,809,677 A | | 3/1989 | Mackin et al. |
| 6,063,020 A | * | 5/2000 | Jones et al. ................... 600/22 |
| 6,224,539 B1 | * | 5/2001 | Jones et al. ................... 600/22 |
| 6,506,147 B2 | * | 1/2003 | Eustace et al. ............... 600/22 |

OTHER PUBLICATIONS

Product Brochure, Hill–Rom Air Shields, Resuscitaire Radiant Warmer, Copyright 1998.

* cited by examiner

*Primary Examiner*—John P. Lacyk
(74) *Attorney, Agent, or Firm*—Roger M. Rathbun

(57) ABSTRACT

An infant warming apparatus that has a canopy vertically movable with respect to an infant resting on an infant between a lower position wherein the apparatus functions as an incubator and an upper position where the apparatus functions as an infant warmer. A radiant heater is located on the canopy and directs infrared energy in a first path towards the infant platform to warm the infant when the canopy is in the upper position. When the canopy is moved to its lower position to act as an incubator, the infrared energy is redirected along a second path that is directed away from the infant platform so as to prevent residual infrared energy that continues to be emitted even after discontinuing power to the radiant heater from affecting the infant as that radiant heater is moved to a position in close proximity to the infant.

15 Claims, 3 Drawing Sheets

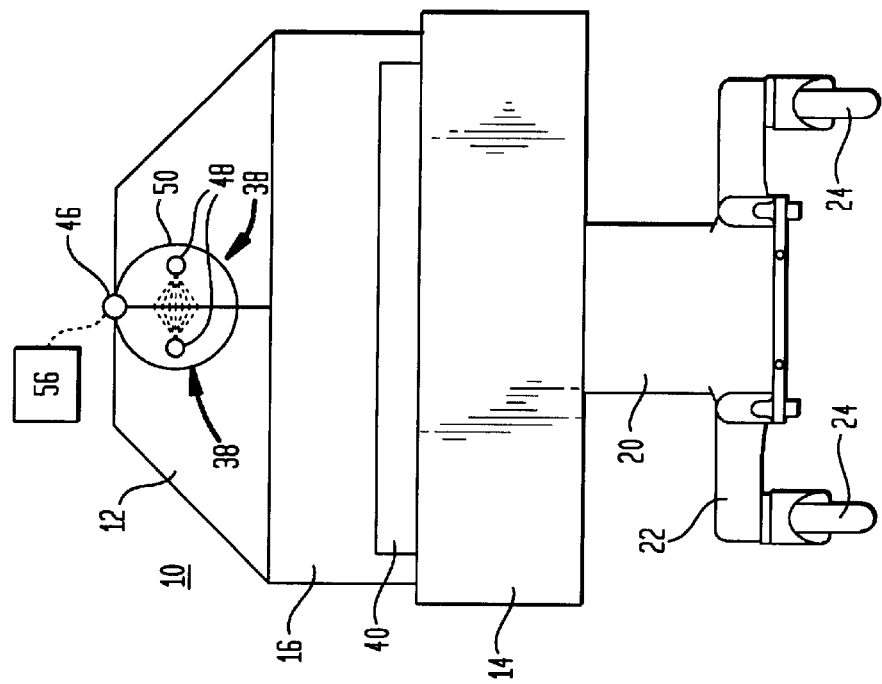
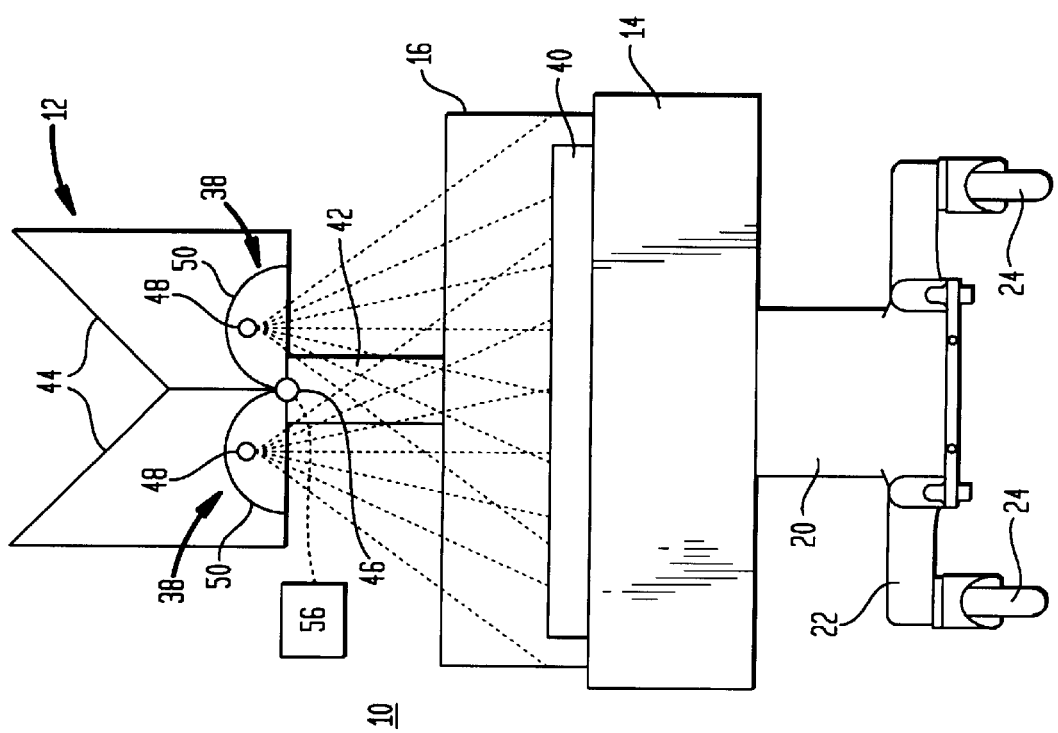

RADIANT FIELD MANAGEMENT FOR INFANT CARE APPARATUS

BACKGROUND

The present invention relates to an infant warming apparatus and, more particularly, to an apparatus for providing the combined functions of an infant incubator and an infant warmer and which includes a radiant heater that can be redirected away from an infant positioned on an infant platform.

There are, of course, many devices or apparatus for the warming of an infant to supply the necessary heat to maintain the infant at a predetermined temperature. Of the various apparatus, there are infant warmers that are basically planar surfaces on which the infant is positioned and which planar surfaces generally include side guards to keep the infant safely within the confines of the apparatus. Infant warmers normally have an overhead radiant heater that is located above the infant and which thus radiates energy in the infrared spectrum to impinge upon the infant to maintain the infant at a warm, predetermined temperature. Since the infant is otherwise totally exposed to the surroundings, there is almost unlimited access to the infant by the attending personnel to perform various procedures on that infant. At typical infant warmer is shown and described in U.S. Pat. No. 5,474,517 of Falk et al and as discussed as prior art to that patent.

There are also infant incubators which are more confined enclosures that contain the infant within an enclosed controlled atmosphere in an infant compartment that provides heat to the infant and also may provide control of humidity in the enclosed environment. These incubators maintain the infant for long periods of time and include handholes to access the infant. Generally, there is, in addition, a larger access door that can be opened to access the infant or to insert or remove the infant to and from the incubator.

Such devices provide a good atmosphere to the infant and control that local environment within which the infant is located, however, it is sometime difficult to perform a wide variety of procedures on the infant due to the somewhat limited access to that infant. A typical infant incubator is shown and described in U.S. Pat. No. 4,936,824 of Koch et al.

At the present, there are also certain infant care apparatus that combine the functions of an infant warmer and an incubator. One such apparatus is shown and described in U.S. Pat. No. 3,858,570 of Beld et al where an overhead canopy or dome is movable between a position where it covers the base to form an environmental chamber and an upper position where the radiant energy is directed toward the infant but the environmental chamber is open to access the infant by the attending personnel.

Similarly, in Jones et al, U.S. Pat. No. 6,224,539, there is disclosed another infant care apparatus that has a canopy containing a radiant heater that can move vertically between a lower position wherein the canopy seats against the periphery of upstanding sides of an infant platform to form, therebetween, an infant compartment for enclosing the infant and an upper position wherein the infant apparatus becomes an infant warmer and the radiant heater is energized to direct the infrared energy downwardly toward the infant resting upon the infant platform.

One of the drawbacks with the type of infant warming apparatus that combines the functions of an infant warmer and an infant incubator, however, is that the radiant heater is obviously brought to an elevated temperature in order to emit the infrared energy and that radiant heater continues to emit the radiant energy for periods of time, possible up to a few minutes or longer, even after the radiant heater has been de-energized.

As such, when the operator de-energizes the radiant heater to convert the infant warming apparatus from an infant warmer to an incubator, the canopy is lowered toward the infant resting on the infant platform while the radiant energy is still being emitted by the radiant heater since the caregiver wants the conversion to take place rather rapidly to maintain the infant in a warmed atmosphere. Thus, the normal lowering of the canopy containing the radiant heater does not allow sufficient time for the radiant heater to cool to fully terminate the emission of radiant energy and, therefore, there is a residual infrared energy that continues to be emitted after electrical power has been shut off to the radiant heater.

Accordingly, there is a need to provide some protection to the infant to prevent that continued emission of radiant energy from reaching the infant and which protection is sufficiently rapid such that the lowering of the canopy containing that radiant heater is not delayed so that the infant warming apparatus can be readily converted from an infant warmer to an incubator in accordance with normal intent of the apparatus.

One viable solution to the problem is shown and described in the aforementioned U.S. Pat. No. 6,224,539 of Jones et al. In that Jones et al patent, a door, or set of doors can be opened and closed and, therefore, when the apparatus is being converted from an infant warmer to an infant incubator, the door(s) automatically close to block the path of the infrared radiant energy from reaching the infant.

While the use of a blocking device is effective, it would be advantageous to have other methods or mechanisms to achieve the protection of the infant from the undesirable infrared radiation reaching that infant under the afore-described conditions.

SUMMARY OF THE INVENTION

Accordingly, the present invention relates to an infant care apparatus that has an overhead canopy containing a radiant heater and where the canopy and heater can be raised and lowered to convert the apparatus between an infant warmer and an infant incubator function. The apparatus has a base with an infant platform formed in the base to support an infant that is to be warmed by the apparatus.

The canopy is movable between and upper position where the radiant heater is energized to direct the radiant heat along a first path toward the infant resting on the infant platform and a lower position where the canopy seats against the peripheral upstanding edges of a plurality of sides of the infant platform to enclose therein, the infant within an infant compartment and the radiant heater is de-energized.

When the infant warming apparatus is intended to be converted from a radiant heater, that is, when the canopy is in its upper position, to an incubator where the canopy is in its lower position, the radiant heater is de-energized and the canopy lowered to that lower position. In order to prevent the continued emission of the radiant energy along the first path toward the infant, however, the infrared energy from the radiant heater is redirected to a second path where it is directed away from the infant platform and the infant so that the infrared energy that continues to be emitted from the radiant heater even after the radiant heater has been de-energized cannot continue to reach an infant resting on the infant platform.

In one embodiment there is a reflector that reflects infrared radiant energy from a heater element toward the infant and the reflector is moved, such as being rotated with respect to the infant platform to redirect the radiant energy to the second path that is directed away from the infant platform. In an alternate embodiment, the canopy itself, containing the heater element and the reflector, is moved, again preferably by rotation with respect to the infant platform, to direct the radiant energy along the second path away from impinging upon the infant resting on the infant platform.

In either embodiment, however, the apparatus causes the redirecting of the infrared energy from a first path where it is directed from the radiant heater toward the infant platform to a second path where the radiant energy is directed away from the infant platform so that the emission of the radiant energy that continues after de-energization of the radiant heater cannot reach the infant.

These and other features and advantages of the present invention will become more readily apparent during the following detailed description taken in conjunction with the drawings herein.

BRIEF DESCRIPTION OF THE DRAWINGS

FIG. 3 is a schematic view of an infant warming apparatus with the radiant energy being directed toward an infant platform; and FIG. 4 is a schematic view of the embodiment of FIG. 3 with the radiant energy redirected to a path that is directed away from an infant platform.

DETAILED DESCRIPTION OF THE INVENTION

Figure 1:
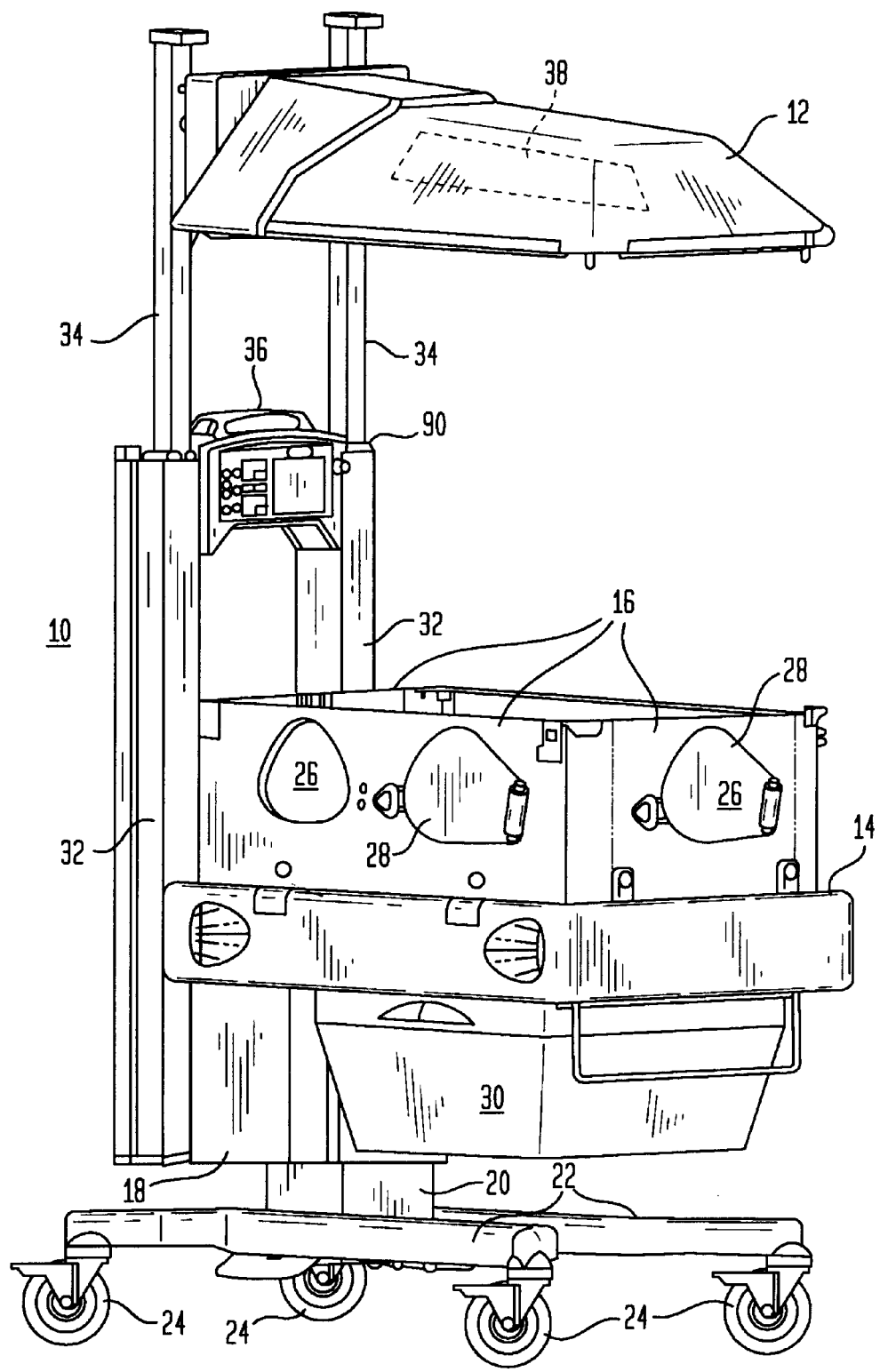
FIG. 1 of a perspective view of the infant warming apparatus constructed in accordance with the present invention wherein the canopy containing a radiant heater is shown in its upper position.
Figure 2:
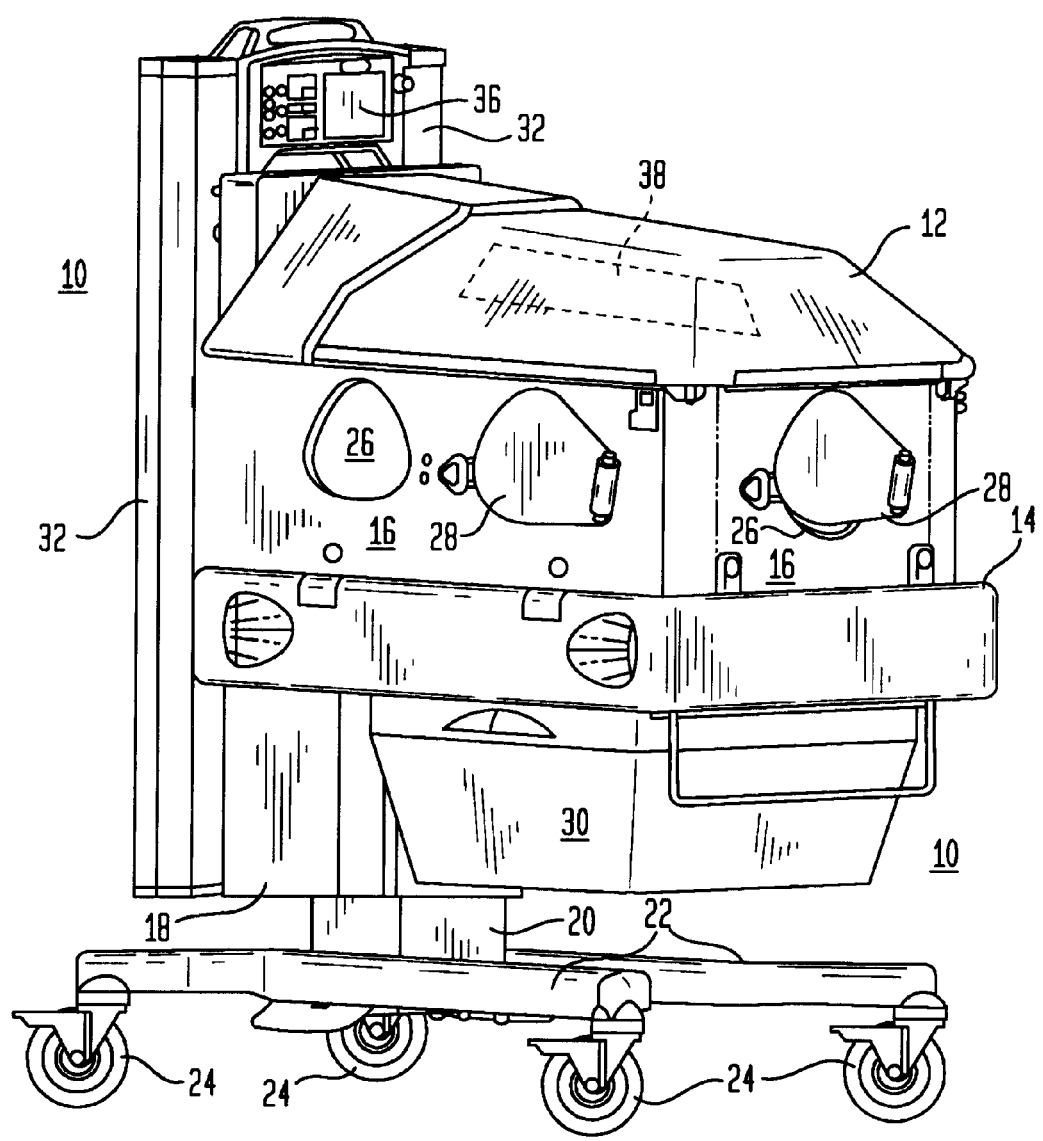
FIG. 2 is a perspective view of the apparatus of FIG. 1 but showing the canopy in its lower position.

Referring now to FIG. 1, there is shown a perspective view of an infant warming apparatus 10 constructed in accordance with the present invention with the canopy 12 in its upper position. Referring also to FIG. 2, there is a perspective view of the infant warming apparatus 10 as shown in FIG. 1 but with the canopy 12 in its lower position. As will be understood, in the FIG. 1 position, the infant warming apparatus 10 acts as an infant warmer with considerable access to the infant for performing interventions on the infant and in the FIG. 2 configuration, the infant warming apparatus 10 acts as an incubator with the infant confined within an infant compartment providing a protective environment and having a controlled atmosphere to provide warmth as well as controlled humidity.

As shown, the infant warming apparatus 10 includes an infant platform 14 that underlies and supports an infant. As is also seen, a plurality of walls 16 are provided to contain the infant safely within the infant warming apparatus 10 and are located at all of the four sides of the infant platform 14. The walls 16 are preferable constructed of transparent plastic material and, as will be explained, cooperate with other components in order to provide an incubator function to the infant warming apparatus 10 when in the FIG. 2 configuration.

The infant platform 14 is mounted to a vertical movable base member 18 which, in the preferred embodiment, is movably affixed to a stationary vertical base member 20, which, in turn, is mounted to a base 22 having wheels 24 for ready movement of the infant warming apparatus 10.

The vertical movable base member 18 is preferably mounted so that the user can adjust the height of the infant platform 14 by raising and lowering the vertical movable base member 18 as desired, thus the infant platform 14 can be adjusted to the preferred height by the user. As further standard features, the walls 16 have handholes 26 to afford access to the infant when in the incubator configuration of FIG. 2, and which generally have doors 28 that can be opened to obtain access to the infant and, of course, closed when the particular intervention has been completed to preserve the desired environment surrounding the infant.

Another convenient feature includes a drawer 30 to retain supplies or other devices needed to carry out some operation on the infant and which is normally located beneath the infant platform 14. Other features include the maneuverability of the walls 16 that are pivotally mounted at their bases to the infant platform 14 such that the doors can be swung outwardly and downwardly and, as a further alternative, can be easily fully removed from the infant platform 14. As such, therefore, when the canopy 12 of the infant warming apparatus 10 is in its upper position as shown in FIG. 1, the walls 16 can be dropped downwardly or removed altogether so that the attending personnel can have unlimited access to an infant resting on the infant platform 14 to perform interventions on that infant.

Further structural components of the infant warming apparatus 10 include stationary frame members 32 that are affixed to the vertical movable base member 18 and, as shown, there are two vertical stationary frame members 32 in the preferred embodiment although there may be only one or there may be further numbers of such members. Two vertical movable frame members 34 are movably fitted into the stationary frame members 32 and which can be moved upwardly and downwardly by the user as will be explained.

A control module 36 is conveniently positioned intermediate the stationary frame members 32 and may include displays of various monitored parameters as well as include the various controls for operation of the functions of the infant warming apparatus 10.

As may now be seen in general, in the operation of the infant warming apparatus 10, the canopy 12, in the preferred embodiment, houses a radiant heater 38 and as will be later explained. The canopy 12 can be moved between its lower position as shown in FIG. 2 and its upper position as shown in FIG. 1 depending upon the mode of operation desired by the user. In the upper position of FIG. 1, the infant care apparatus 10 functions as an infant warmer where there is full access to the infant and where the overhead radiant heater 38 supplies heat to maintain the infant with sufficient warmth.

In the lower position of FIG. 2, the infant warming apparatus 10 functions as a normal incubator, since the outer periphery of the infant canopy 12 fits fully over the upper edges of the walls 16 to form therein, an infant compartment that is provided with warm air and controlled humidity in the normal functioning of an incubator.

Thus, in the operation of the infant warming apparatus, when the canopy 12 and, of course, the heater 38 are in the upper position as shown in FIG. 1, the radiant heater 38 can be energized and the infrared energy is directed along a first path from the radiant heater 38 toward the infant platform 14 to supply heat to an infant resting on that infant platform 14. When the caregiver decides to change the function of the infant warming apparatus from an infant warmer function to an incubator function, the radiant heater 38 is de-energized by terminating the power to that radiant heater 38 so that the radiant heater 38 is assured of being off when the canopy 12 is moved downwardly in the direction toward an infant situated on the infant platform 14.

A specially designed interlock system can also be provided as a safety measure to assure that the radiant heater 38 has, in fact, been fully de-energized before the canopy 12 can fully move downwardly and that system is shown and described in U.S. Pat. No. 6,063,020 of Jones et al and the disclosure of that patent is incorporated herein by reference.

As stated, however, even if it is assured that the radiant heater 38 is off, that is, the power to the radiant heater has been terminated, due to the elevated temperatures of the radiant heater 38, there is still an emission of infrared energy from the heated surface of the radiant heater 38 and that radiation can reach the infant and become problematic as the canopy 12 is lowered since the radiant heater 38 physically approaches close to the infant.

Thus, again, as explained, one means of preventing that radiant energy from reaching the infant is to physically block that path of the radiant infrared energy otherwise passing from the radiant heater 38 to the infant platform 14 by means of a blocking member such as a door or doors and such system is shown and described in U.S. Pat. No. 6,231,499 of Jones and the disclosure of that patent is incorporated herein by reference.

In any event, the present invention is an alternative solution to that disclosed in the Jones patent '499 patent. With the present invention, the path of the radiant energy proceeds along a first path from the radiant heater 38 toward the infant platform 14 when the infant is being heated. Thus, when the radiant heater 38 is de-energized, the mechanism of the present invention re-directs that path of the radiant energy from the radiant heater 38 to a second path that is directed away from the infant platform 14 so that such residual infrared energy is directed along a second path that does not reach the infant positioned on the infant platform 14.

Turning now to FIGS. 3 and 4, there are shown schematic views of one embodiment of the present invention and like numbers have been used where there are corresponding features of FIG. 1 and 2. In addition to the features and components shown and described in FIGS. 1 and 2, the schematic views of FIGS. 3 and 4 include a mattress 40 that is positioned on top of the infant platform 14 for the comfort of the infant positioned thereon.

The canopy 12 is shown affixed to a vertical frame member 42 that extends upwardly from the base 22 and the canopy 12 is, in the embodiment shown, comprised of two canopy sections 44 positioned side by side and pivotally mounted to the vertical frame member 42 at a pivot mounting 46. The construction of the two canopy sections 44 and the pivotal mounting thereof to the vertical frame member 42 can be readily carried out by conventional means and may be constructed somewhat similar in function to the canopy sections shown and described in Donnelly et al, U.S. Pat. No. 5,453,077.

Accordingly, as seen in FIGS. 3 and 4, there is a heater element 48 mounted to each of the canopy sections 44 so as to provide a source of infrared radiation upon energization by a source of controllable electricity. Also affixed to each of the canopy sections 44 is a reflector 50 so that the infrared energy emitted by the heater elements 48 can be directed along a first path, indicated by the dotted lines in FIG. 3, from the radiant heaters 38 toward the infant platform 14 where the infrared energy impinges upon an infant resting on the infant platform 14 to provide heat to the infant.

Thus, in the FIG. 3 position of the canopy 12, that is, in its upper position, the infant warming apparatus 10 is acting as an infant warmer and the radiant heaters 38 are both directing the infrared energy along the first paths toward the infant platform 14 when that energy provides heat to an infant resting on the infant platform 14.

In FIG. 4, the infant warming apparatus 10 is acting as an infant incubator since the canopy in FIG. 4 is positioned in its lower position, thereby enclosing therein the infant compartment to contain the infant in a climate controlled, protective environment. Thus, between the FIG. 3 and FIG. 4 positions of the canopy 12, the canopy sections 44 have both been rotated about the pivot mounting 46 so as to come together and form a combined canopy for fitting over the infant platform 14 to form an infant compartment for containing the infant As can be seen in FIG. 4, the path of the infrared energy emitted by each of the heater elements 48 and reflected by the reflectors 50 has been redirected from the first path shown in FIG. 3 toward the infant platform 14 and is now directed in a second path, indicated by the dotted lines of FIG. 4, in a direction that is away from the infant platform 14 and therefore the incidental or remaining radiant energy emitted from the de-energized heater element 48 is not directed toward the infant, and therefore, the infrared energy that continues to be emitted from the radiant heater 38 does not create a hazard to the infant even where the canopy 12 is moved to such a close position with respect to the infant platform 14.

It will be seen that the redirecting of the infrared radiation emitted from the radiant heater 38 can be by a manual movement of canopy sections 44 or, alternatively, the movement or redirecting of the radiant heater 38 can be carried out by some motive means such as an electric motor 56 shown schematically in FIGS. 3 and 4.

Those skilled in the art will readily recognize numerous adaptations and modifications which can be made to the infant care apparatus of the present invention which will result in an improved infant protective system, yet all of which will fall within the scope and spirit of the present invention as defined in the following claims. Accordingly, the invention is to be limited only by the following claims and their equivalents.

I claim:

1. An infant warming apparatus, said infant warming apparatus comprising an base having an infant platform on which an infant is adapted to be positioned, a canopy mounted to said base and being movable between a lower position wherein said canopy fits over the infant platform to form an infant compartment enclosing an infant and an upper position where said canopy is elevated with respect to the infant platform and said infant compartment is open, at least one radiant heater affixed to said canopy, said at least one radiant heater being operable when said canopy is in said upper position to direct infrared energy along a first path toward said infant platform, and a mechanism to move the radiant heater to redirect the infrared energy from the first path to a second path that is directed away from the infant platform.

2. An infant warming apparatus as defined in claim 1 wherein said at least one radiant heater comprises a plurality of radiant heaters.

3. An infant warming apparatus as defined in claim 1 wherein said at least one radiant heater comprises a radiant heater element and a reflector to direct and concentrate infrared energy from said radiant heater element along said first path toward said infant platform.

4. An infant warming apparatus as defined in claim 3 wherein said reflector of said at least one radiant heater is rotatably affixed to said canopy and said mechanism to redirect the radiant energy comprises a means to rotate the reflector with respect to said canopy.

5. An infant warming apparatus as defined in claim 1 wherein said at least one radiant heater comprises two heaters, each having a reflector.

6. An infant warming apparatus as defined in claim 4 wherein said means to rotate the reflector comprises a motor.

7. An infant warming apparatus as defined in claim 1 wherein said canopy is rotatably affixed to said base and said mechanism to move the radiant heater to redirect the radiant energy comprises a means to rotate the canopy with respect to said infant platform.

8. An infant warming apparatus as defined in claim 7 wherein said canopy comprises two canopy sections, each having a radiant heater affixed hereto and both of said canopy sections being rotatably affixed to said base.

9. An infant warming apparatus as defined in claim 8 wherein each of said radiant heaters comprises a radiant heater element and a reflector.

10. A method of protecting an infant positioned on an infant platform in an infant warming apparatus from undesirable infrared radiation, said method comprising the steps of:

providing a canopy that is movable vertically with respect to the infant platform, providing a radiant heater affixed to the canopy energized by a source of electricity to emit infrared energy, directing the infrared energy emitted by the radiant heater along a first path to impinge upon the infant platform, deactivating the source of electricity that is energizing the radiant heater, and moving the radiant heater to redirect the path of infrared energy from the radiant heater to a second path that is directed away from the infant platform.

11. A method as defined in claim 10 wherein said step of providing a radiant heater comprises providing a heater element and a reflector to direct infrared energy from the heater element toward the infant platform.

12. A method as defined in claim 11 wherein said step of moving the radiant heater to redirect the path of infrared energy comprises repositioning the reflector to redirect the path of infrared energy to the second path.

13. A method as defined in claim 10 said step of providing a canopy comprises providing a canopy that is rotatable along an axis that is generally parallel to the plane of the infant platform.

14. A method as defined in claim 13 wherein said step of moving the radiant heater to redirect the path of infrared energy comprises rotating the canopy along the axis to redirect the path of infrared energy to the second path.

15. A method as defined in claim 10 wherein the step of providing a radiant heater comprises providing a plurality of radiant heaters.

* * * * *